(12) United States Patent
Schaeffer et al.

(10) Patent No.: US 10,832,122 B2
(45) Date of Patent: Nov. 10, 2020

(54) CONTINUOUS DECODING DIRECT NEURAL INTERFACE WHICH USES A MARKOV MIXTURE OF EXPERTS

(71) Applicant: COMMISSARIAT A L'ENERGIE ATOMIQUE ET AUX ENERGIES ALTERNATIVES, Paris (FR)

(72) Inventors: Marie-Caroline Schaeffer, Grenoble (FR); Tetiana Aksenova, Saint Egreve (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 755 days.

(21) Appl. No.: 15/615,080

(22) Filed: Jun. 6, 2017

(65) Prior Publication Data

US 2018/0005105 A1    Jan. 4, 2018

(30) Foreign Application Priority Data

Jun. 30, 2016   (FR) ..................... 16 56246

(51) Int. Cl.
| | |
|---|---|
| *G06N 3/04* | (2006.01) |
| *A61F 2/72* | (2006.01) |
| *G06F 3/01* | (2006.01) |
| *G06T 7/277* | (2017.01) |
| *G06K 9/62* | (2006.01) |
| *G06N 3/063* | (2006.01) |

(52) U.S. Cl.
CPC ............ *G06N 3/0427* (2013.01); *A61F 2/72* (2013.01); *G06F 3/015* (2013.01); *G06K 9/6297* (2013.01); *G06N 3/063* (2013.01); *G06T 7/277* (2017.01)

(58) Field of Classification Search
CPC ...... G06N 3/0427; G06N 3/063; G06T 7/277; A61F 2/72; G06F 3/015; G06K 9/6297
See application file for complete search history.

(56) References Cited

U.S. PATENT DOCUMENTS

| | | |
|---|---|---|
| 2013/0165812 A1 | 6/2013 | Aksenova et al. |
| 2014/0365163 A1* | 12/2014 | Jallon ............... A61B 5/1116 702/141 |

OTHER PUBLICATIONS

Xu et al, Generalized PLS regression, 2001, Journal of Chemometrics (Year: 2001).*

(Continued)

*Primary Examiner* — Austin Hicks
(74) *Attorney, Agent, or Firm* — Oblon, McClelland, Maier & Neustadt, L.L.P.

(57) ABSTRACT

A method of continuous decoding of motion for a direct neural interface. The method of decoding estimates a motion variable from an observation variable obtained by a time-frequency transformation of the neural signals. The observation variable is modelled using a HMM model whose hidden states include at least an active state and an idle state. The motion variable is estimated using a Markov mixture of experts where each expert is associated with a state of the model. For a sequence of observation vectors, the probability that the model is in a given state is estimated, and from this a weighting coefficient is deduced for the prediction generated by the expert associated with this state. The motion variable is then estimated by combination of the estimates of the different experts with these weighting coefficients.

13 Claims, 3 Drawing Sheets

(56) References Cited

OTHER PUBLICATIONS

Wikipedia, semi-supervised learning, Jun. 18, 2016, wikipedia.com (Year: 2016).*
French Preliminary Search Report dated Mar. 2, 2017 in French Application 16 56246 filed on Jun. 30, 2016 (with English Translation of Categories of Cited Documents).
Shalom Darmanjian et al. "Bimodal Brain-Machine Interface for Motor Control of Robotic Prosthetic", Proceedings of the 2003 IEEE/RSJ Intl. Conference on Intelligent Robots and Systems, Oct. 27, 2003, pp. 6.
Marina Meila et al. "Learning Fine Motion by Markov Mixtures of Experts," Advances in Neural Information Processing Systems 8 (1567), Nov. 1995, pp. 7.
Rasmus Bro "Multi-way analysis in the food industry: models, algorithms, and applications," Amsterdam: Universiteit van Amsterdam, 1998, pp. 312.

* cited by examiner

CONTINUOUS DECODING DIRECT NEURAL INTERFACE WHICH USES A MARKOV MIXTURE OF EXPERTS

TECHNICAL FIELD

The subject of this invention relates to the field of direct neural interfaces, also known as BCIs (Brain Computer Interfaces) or BMIs (Brain Machine Interfaces). It is also applicable in particular to direct neural command of a machine, such as an exoskeleton or a computer.

STATE OF THE PRIOR ART

Direct neural interfaces use electro-physiological signals emitted by the cerebral cortex to create a command signal. These neural interfaces have been the subject of much research, in particular with the aim of restoring motor function to paraplegic or tetraplegic subjects using a powered prosthesis or orthosis.

Neural interfaces may be invasive or non-invasive in character. Invasive neural interfaces use intra-cortical electrodes (that is, which are implanted in the cortex) or cortical electrodes (arranged at the surface of the cortex) which in the latter case receive electrocorticographic (ECoG) signals. Non-invasive neural interfaces use electrodes placed on the scalp to receive electroencephalographic (EEG) signals. Other types of sensors have also been envisaged, such as magnetic sensors which measure the magnetic fields induced by the electrical activity of the brain's neurons. These are then called magnetoencephalographic (MEG) signals.

Direct neural interfaces advantageously use ECoG-type signals which offer the advantage of a good compromise between bio-compatibility (matrix of electrodes implanted at the surface of the cortex) and the quality of the signals gathered.

The ECoG signals thus measured must be processed in order to estimate the trajectory of motion desired by the subject and to deduce from this the command signals for the computer or for the machine. For example, when command of an exoskeleton is involved the BCI interface estimates the trajectory of motion desired from measured electro-physiological signals, and deduces from this the command signals which allow the exoskeleton to reproduce the trajectory in question. Similarly, when command of a computer is involved, the BCI estimates, for example, the desired trajectory of a pointer or a cursor from electro-physiological signals and deduces the cursor/pointer command signals from this.

The estimation of the trajectory or more precisely, that of the kinematic parameters (position, speed, acceleration) is referred to in the literature as neural decoding. In particular, neural decoding allows motion (of a prosthesis or of a cursor) to be commanded from ECoG signals.

When ECoG signals are continuously acquired, one of the main difficulties in decoding lies in the asynchronous nature of the command, or in other words in discriminating between phases during which the subject is actually commanding a motion (active periods) and phases in which they are not commanding one (idle periods).

In order to overcome this difficulty direct neural interfaces, known as synchronous interfaces, only allow the possibility of commanding a motion during well-determined time windows (for example, time intervals which periodically succeed each other), signaled to the subject by an external indicator. The subject can then only command the motion during these time windows, which proves to be prohibitive in most practical applications.

More recently, continuous decoding direct neural interfaces have been proposed in the literature. The article by M. Velliste et al., entitled "Motor cortical correlates of arm resting in the context of a reaching task and implications for prosthetic control" published in The Journal of Neuroscience, 23 Apr. 2014, 34(17), pp. 6011-6022, in particular describes a direct neural interface wherein the rest periods (idle state) are detected by LDA (Linear Discriminant Analysis) from the emission frequency of action potentials (neuron firing rate). The kinematic parameters are estimated during the active periods by means of a state-transition model, the states being predicted by means of a so-called Laplace-Gauss filter. The results, however, were obtained for matrices of micro-electrodes and cannot be reproduced for conventional cortical electrodes. Furthermore, the switching events between idle periods and active periods are expressed as discontinuities in the decoding of the motion and therefore as jerks throughout the trajectory.

Another approach was proposed in the article by L. Srinivasan et al. entitled "General-purpose filter design for neural prosthetic devices" published in J. Neurophysiol. Vol 98, pp. 2456-2475, 2007. This article describes a continuous decoding direct neural interface wherein the sequence of active states and idle states is generated by a 1st order Markov model. A Switching Kalman Filter (SKF) whose observation matrices and transition matrices depend on the hidden switching variable (active state/idle state) allows the kinematic parameters of the motion to be estimated. This type of direct neural interface has been used to control a wheelchair using EEG signals based on simulation data, but has not been tested for ECoG signals. In addition, the detection of state (active state/idle state) is sometimes subject to error (high level of false positives and false negatives).

Finally, the aforementioned direct neural interfaces were developed to decode the motion of a single limb of a subject. They are therefore not suited for command of an exoskeleton with several limbs, in particular for tetraplegic, paraplegic or hemiplegic subjects. This limits their field of application substantially.

The aim of this invention is consequently to propose a method for continuous decoding of motion for a direct neural interface, and which exhibits a low rate of false active state detection and which allows decoding without discontinuity of motion, from a subject's ECoG signals. Another aim of the present invention is to allow decoding of the motion of several limbs from a subject's ECoG signals.

DESCRIPTION OF THE INVENTION

The present invention is defined by a method of continuous decoding of motion for a direct neural interface which acquires neural signals using a plurality of electrodes, characterised in that a command variable, y(t), is estimated which represents kinematic variables of the motion, using a mixture of experts, where each expert is associated with one of the hidden states of a HMM model which models an observation variable represented by an observation vector, x(t), where the HMM model comprises at least one active state and one idle state, said method comprising:

a calibration phase for estimating the parameters of the HMM model and of a linear prediction parameter of each expert;

pre-treatment of neural signals said treatment including a time-frequency transformation over a moving observation window, in order to obtain a sequence of observation vectors, x[1:t]

estimation (230) of the mixture coefficients ($g_k(t), k=1,\ldots,K$) of the various experts from the probability of said sequence of observation vectors ($P(x[1:t])$) and from the probability of the respective states associated with these experts, given said sequence ($P(z_k(t)=1|x[1:t])$);

estimation by each expert, $\mathcal{E}_k$, of said motion variable from the current observation vector (x(t)) and from the linear prediction parameter of said expert;

combination of estimates of the various experts using the mixture coefficients in order to provide an estimate of the command variable.

According to one embodiment alternative, the hidden states of the HMM model comprise, for each element of a plurality of elements, commanded respectively by a component of the motion variable, an active state during which said element is operated and an idle state during which said element is idle.

The hidden states of the HMM module may further comprise, for each of said elements, a motion preparation state which immediately succeeds an idle state and which immediately precedes an active state of said element.

Advantageously, during the calibration phase the HMM model parameters and linear parameters of the experts are obtained from a sequence of observation vectors and from a sequence of motion variable measurements, in accordance with a supervised learning method.

The linear parameters of the experts are obtained by means of a partial least squares regression or even by means of a generalised partial least squares regression.

Alternatively, during the calibration phase the parameters of the HMM model and the linear parameters of the experts are obtained from a sequence of observation vectors and from a sequence of motion variable measurements, according to a semi-supervised learning method.

In this case the linear parameters of the experts may be obtained using an expectation-maximisation algorithm.

The time-frequency transformation is advantageously decomposition into wavelets.

The mixture coefficient $g_k(t)$ associated with the expert $\mathcal{E}_k$ is obtained through $$g_k(t) = \frac{P(z_k, x[1:t])}{P(x[1:t])}$$

where $P(x[1:t])$ is the observation probability of the sequence of observation vectors and $P(z_k, x[1:t])$ is the state probability associated with the expert, given the sequence observed, with the probabilities $P(x[1:t])$ and $P(z_k, x[1:t])$ being obtained using a forward algorithm.

Advantageously, the estimate $\hat{y}_k(t)$ of the motion variable by the expert $\mathcal{E}_k$ is obtained through $\hat{y}_k(t)=\beta_k x(t)$ where $\beta_k$ is a matrix of size N×M where M is the dimension of the observation vectors and N the dimension of the command variable.

The neural signals are typically electro-cortical signals (ECoG) signals.

BRIEF DESCRIPTION OF THE ILLUSTRATIONS

Other characteristics and advantages of the invention will become clear after reading a preferred embodiment of the invention with reference to the attached figures among which:

DETAILED DESCRIPTION OF PARTICULAR EMBODIMENTS

We will consider below a direct neural interface with continuous decoding of motion in the sense defined above. The decoding is continuous in the sense that it is carried out over the passage of time without being synchronised with an external stimulus. The interface acquires neural signals, typically ECoG signals from a matrix of electrodes implanted beforehand at the surface of a subject's cortex. The direct neural interface serves to decode the motion from the neural signals so as to command motion of an external element. The term "external element" means, in a non-restrictive manner, all or part of a prosthesis, an orthosis, an exoskeleton, a wheelchair or an effector. It also means, in a non-restrictive manner, a visual symbol such as a cursor or an icon whose motion is usually controlled by a HMI (Human Machine Interface).

The neural signals acquired by the interface undergo pre-treatment (details below) in order to provide an observation variable of dimension M which is dependent on the time, referred to as x(t) where t is an integer representing a discretised time. This variable represents an observation of the characteristics of the measured neural signals, from which it is possible to estimate the kinematic parameters. The term kinematic parameters means, in particular, the position, the speed and/or the acceleration along the trajectory.

The concept upon which the invention is based is decoding of the motion by means of Markov mixtures of experts. Estimation by Markov mixtures of experts (or MME) is based on a Hidden Markov Model (or HMM), where an estimator (called an expert) is associated with each hidden state of the model. A presentation of an estimation method using Markov mixture of experts can be found in the article by M. Meila et al. Entitled "Learning fine motion by Markov mixtures of experts" published in Advances in Neural Information Processing Systems 8 (1567), pp. 1003-1009.

Figure 1:
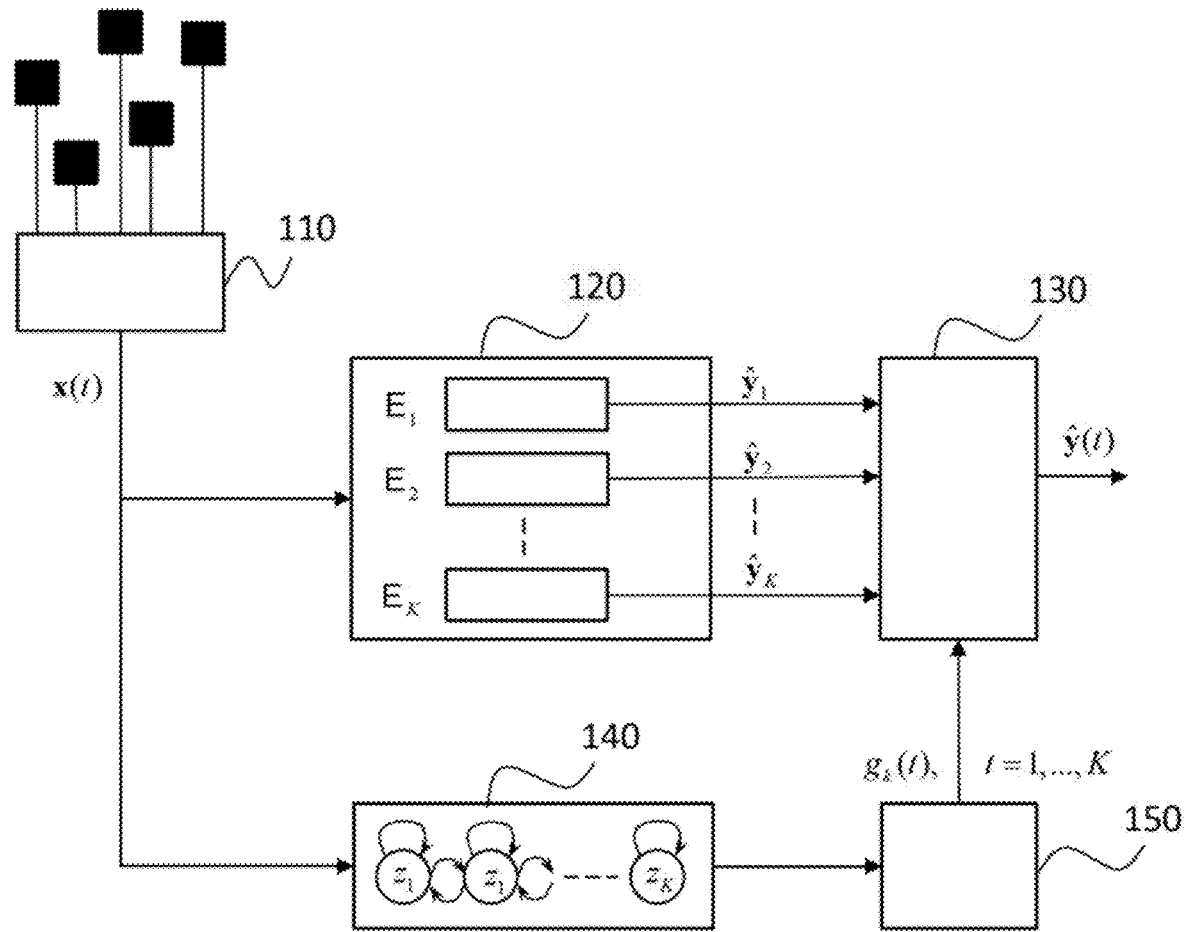
FIG. 1 shows a schematic of the principle of continuous decoding of motion by Markov mixture of experts used in this invention.

FIG. 1 shows a schematic of the principle of continuous decoding of motion by Markov mixtures of experts.

The Markov mixture of experts makes use, on the one hand, of a hidden state automation (or HMM model) 140 which can take K possible states, and on the other hand a plurality K of estimators, 120, where each estimator is associated with a hidden state.

The different experts' estimates are combined in a combination module (gating network) 130 to give an estimate, ŷ(i), of the variable to be explained, y(i), here the kinematic parameters of the motion, from the observation x(t) which represents the characteristics of the neural signals at the instant t, detected using the electrodes 105. Hereafter the input variable x(t) is assumed to be of dimension M and the response y(t) is assumed to be of dimension N.

The mixture of experts assumes that the starting space, that is, the space X in which the input variable takes its values may be partitioned into a plurality K of regions, that is $$X = \bigcup_{k=1}^{K} X_k.$$

For each region $X_k$ there corresponds a model of the prediction of the variable y(t) by the variable x(t). The prediction model, or expert, is defined by a local function $f_k$ of the region $X_k$ from the starting space X to the end space Y.

In a conventional mixture of experts (ME), the dependence of the variable y(t) as a function of x(t) is modelled over the entire starting space; in other words the variable to be explained is assumed to behave according to the model:

$$y(t) = \sum_{k=1}^{K} z_k(t) f_k(x(t)) + \eta(t) \quad (1)$$

where $z_k(t)=1$ when the variable y(t) is generated by the model $f_k$ (and $z_k(t)=0$ if not) and where $\eta(t)$ to is a noise vector of size N here assumed to be Gaussian.

The estimate of the variable to be explained can be broken down into the following form:

$$\hat{y}(t) = E(y(t) \mid x(t)) = \sum_{k=1}^{K} E(y(t), z_k(t) = 1 \mid x(t)) = \sum_{k=1}^{K} P(z_k(t) = 1 \mid x(t)) E(y(t) \mid x(t), z_k(t) = 1) \quad (2)$$

In other words:

$$\hat{y}(t) = E(y(t) \mid x(t)) = \sum_{k=1}^{K} g_k(t) \hat{y}_k(t) \quad (3)$$

where $\hat{y}_k(t)=E(y(t)|x(t),z_k(t)=1)$ is the estimate obtained by the expert $\mathcal{E}_k$ and $g_k(t)=P(z_k(t)=1|x(t))$, k=1, ... K are mixture coefficients. The coefficient $g_k(t)$ expresses the conditional probability that the variable to be explained was generated by the model $f_k(t)$ given that x(t) was observed. The weighting coefficients (or mixture coefficients) verify the property:

$$\sum_{k=1}^{K} g_k(t) = 1 \quad (4)$$

The mixture coefficients $g_k(t)$ are estimated by module 150 from the sequence of observation vectors as explained later. These mixture coefficients are supplied to the combination module 130.

The models $f_k$ of the experts are advantageously chosen to be linear, in other words $f_k(x(t))=\beta_k x(t)$ where $\beta_k$ is a matrix of size N×M. In this case the estimate using mixture of experts is simply written as:

$$\hat{y}(t) = \sum_{k=1}^{K} g_k(t) \beta_k x(t) \quad (5)$$

It is now assumed that the sequence of observations x[1:t]={x(1),x(1),x(2), ... , x(t)} is modelled by an underlying Markov method, of order 1, and continuous emission. At each instant t, the hidden states automation can take K distinct states $\{z_1,z_2,\ldots,z_K\}$ which correspond respectively to the cases $z_k(t)=1$, k=1, ... , K. The state of the automation at the instant t depends on its state at, the preceding instant, t−1, (Markov model of order 1) as well as, on the probability of the transition between these states. The sequence of hidden states is consequently fully characterised by the initial probabilities of occupation of the different hidden states and of the matrix of probabilities of transition between states. The probability distribution of the observation variable x(t) at the instant t depends only on the state z(t) of the HMM automation at that instant. The conditional probability P(x(t)|z(t)) of the observation variable is called the emission probability. The probabilities that the automation is initially in the K different states, the probabilities of transition between states and the emission probabilities are called the HMM model parameters.

In a Markov mixture of experts it is assumed that the mixture coefficients depend on the sequence of observations x[1:t], in other words:

$$g_k(t) = P(z_k(t)=1|x[1:t]) \quad (6)$$

The mixture coefficient can be determined using Bayes rule:

$$P(z_k(t) = 1 \mid x[1:t]) = \frac{P(z_k(t) = 1, x[1:t])}{P(x[1:t])} \quad (7)$$

where the probabilities P(x[1:t]) and P($z_k$(t)=1,x[1:t]) can be obtained recursively using the forward algorithm from the HMM model parameters, in a manner which is known per se.

The parameters of the HMM model and the parameters $\beta_k$ of the different experts can be estimated during a calibration phase, using a supervised or semi-supervised estimation method.

A supervised estimation method may be implemented if the following are available; a complete set of learning data, namely a sequence of observations (sequence of neural signal characteristics), x[1:t], the sequence of kinematic parameters y[1:t] is well as the sequence of corresponding states z[1:t].

The HMM automation and the K experts are then trained independently of each other. For example, the matrix of probabilities of transition between states of the HMM automation can be estimated by counting the frequencies of transitions between states in the learning sequence z[1:t]. Similarly, the emission probabilities of the HMM automation can be estimated from sequences z[1:t] and x[1:t]. The expert $\mathcal{E}_k$ can be trained on the basis of relevant sub-sequences {$x_k$} and {$y_k$} extracted respectively from x[1:t] and y[1:t] where {$x_k$}={$x_k \in$x[1:t]|$z_k(\tau)$=1} and {$y_k$}={$y_k \in$x[1:t]|$z_k(\tau)$=1}. The matrix $\beta_k$ can be estimated by linear regression or by linear PLS linear regression over these sub-sequences. Alternatively, the matrix $\beta_k$ can be obtained by multivariate PLS or NPLS (N-way PLS) regression from these sub-sequences. A detailed description of the NPLS regression method can be found in the thesis by R. Bro entitled "Multi-way analysis in the food industry: models, algorithms and applications", 1998. The multi-variate PLS method was applied to the calculation of the model for predicting the trajectories in a BCI interface as described in the article by A. Eliseyev and T. Aksenova entitled "Recursive N-Way Partial Least Squares for Brain-Computer Interface" published in PLOS One, July 2013, vol. 8, no. 7, e69962.

A semi-supervised method of estimation may be implemented when the sequences x[1:t], y[1:t] and z[1:t] are only partially known. In this case, the parameters of the HMM automation and the matrices $\beta_k$ of the experts may be estimated by an Expectation-Maximisation algorithm.

Where appropriate the parameters of the HMM model and the parameters $\beta_k$ of the different experts can be estimated during a calibration phase, using a non-supervised learning method. The term non-supervised learning means that estimation of the parameters is carried out without knowledge of the sequence of states, represented by the vector z=z[1:t]. The estimate is obtained from an expectation-maximisation a algorithm by iterative alternation of steps for evaluating the expectation (step E) of the likelihood and steps for maximisation of the likelihood, as explained below.

If the term $B=\beta_1, \ldots, \beta_K$ is used for the set of expert matrices and A for the set of HMM model parameters (vector of initial probabilities of the different states and transition matrix), and it $\Omega$=A,B for the set of all of the parameters, a function $Q$ is defined by:

$$Q(\Omega, \hat{\Omega}, X, Y) = E[L_c(\Omega, X, Y, z) | \Omega = \hat{\Omega}, X, Y] \quad (8)$$

where X=x[1:t], Y=y[1:t], where $\hat{\Omega}$ is a prior estimate of $\Omega$ and $L_c$ is the log-likelihood:

$$L_k(\Omega, X, Y, z) = \ln P(X, Y, z | \Omega) \quad (9)$$

The purpose of step E, at iteration (i+1), referred to as $E^{(i+1)}$, is to calculate the expectation of this likelihood in terms of this sequence of states z. That is:

$$E[L_c(\Omega, X, Y, z) | \Omega = \hat{\Omega}^{(i)}, X, Y] = \sum_z L_c(\Omega, X, Y, z) P(z | \Omega = \hat{\Omega}^{(i)}, X, Y) \quad (10)$$

where $\hat{\Omega}^{(i)}$ is an estimate of the parameters obtained in the previous step.

This expectation is calculated for each sequence of states z when the estimation method is non-supervised (and over the missing sequences when the learning method is semi-supervised, to supplement the known, sequences).

The purpose of step M at iteration (i+1), referred to as $M^{(i+1)}$, is to seek the maximum likelihood $\hat{\Omega}^{(i+1)}$, given the values $Q(\Omega, \hat{\Omega}^{(i)}, X, Y)$ obtained at step $E^{(i+1)}$, that is:

$$\hat{\Omega}^{(i+1)} = \arg\max_\Omega (Q(\Omega, \hat{\Omega}, X, Y)) \quad (11)$$

with this estimate, $\hat{\Omega}^{(i+1)}$, being used in turn in step $E^{(i+2)}$.

Thus one moves closer and closer to a local optimum of $\hat{\Omega}$, stopping after a pre-determined number of iterations. By starting from different initial parameter values, a global optimum of $\hat{\Omega}$ can be obtained.

Irrespective of the learning method used during the calibration phase, it is important to note that the continuous decoding method is based on a specific definition of the states of the HMM automation. Advantageously, these states will include an idle state, an active state, and, optionally, a motion preparation state. In the idle state the subject is not commanding the external element (a prosthetic or a cursor, for example). Conversely, in the active state the subject is commanding the motion of this element. The preparatory state is a state immediately preceding the active state and immediately succeeding the idle state, during which the characteristics of the neural signals are neither those of the idle state nor those of the active state.

When the direct neural interface has to command the motion of several external elements (several limbs of an exoskeleton, for example), the states of the HMM automation comprise the aforementioned states (idle, active and, optionally, preparatory) for each of these elements. In other words, if the direct neural interface has to command the motion of L elements, the number of states will be $K=2^L$ or $3^L$ (if the preparatory states are envisaged).

The weighting of the predictions of the K experts associated with the different states prevents jerks in the motion. Furthermore it has been shown that decoding by Markov mixture of experts substantially reduced the level of false positives (motion command generated, whereas the subject is in reality in an idle state) and the rate of false negatives (no motion command, whilst the subject in reality wishes to perform a motion).

Figure 2:
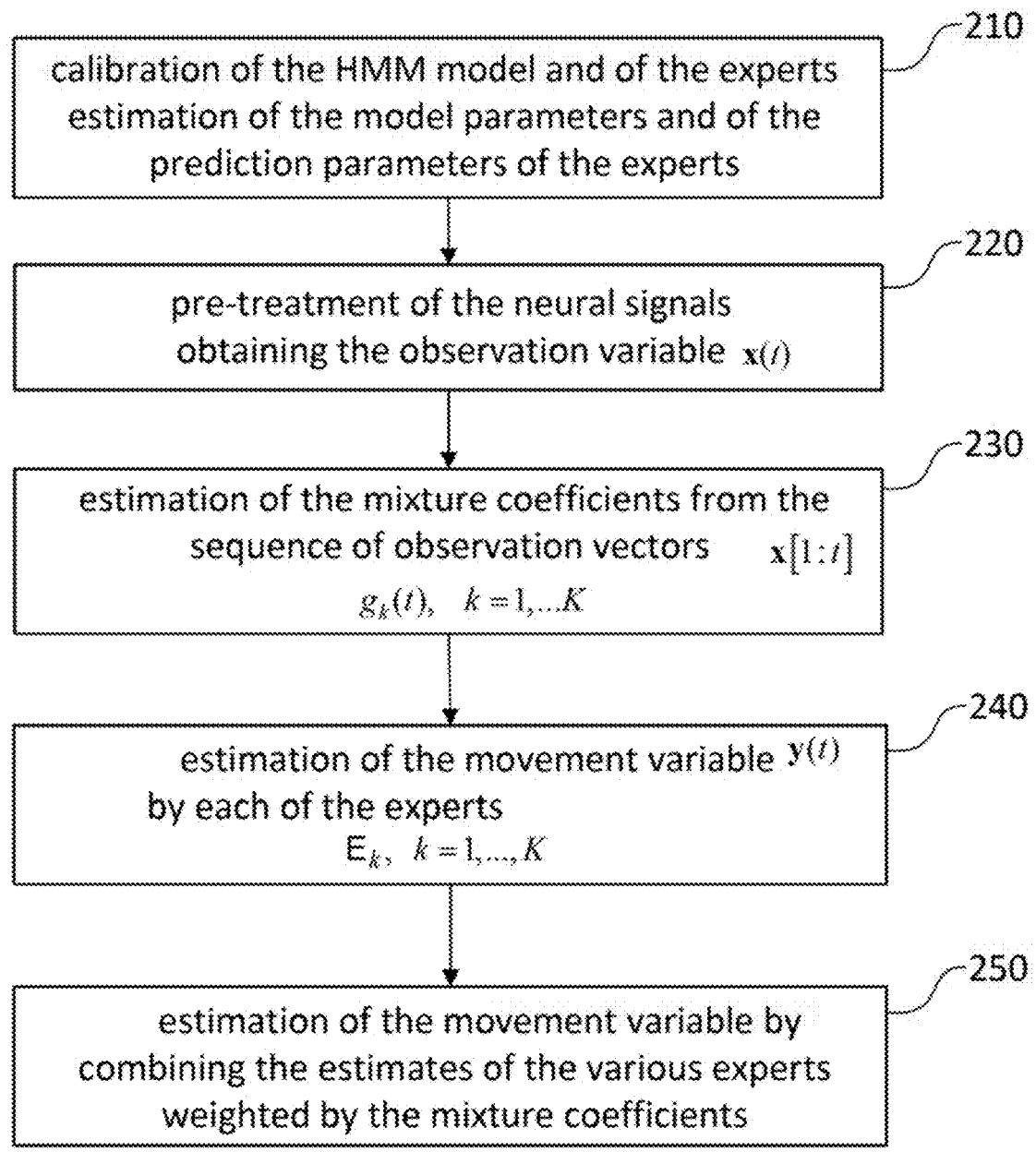
FIG. 2 shows, in the form of a flowchart, the method of continuous decoding of motion for a direct neural interface according to one embodiment of the present invention.

FIG. 2 shows, in the form of a flowchart, the method for continuous decoding of motion implemented for a direct neural interface according to one embodiment of the present invention;

At step 210, a calibration of the HMM model and of the experts is performed, More precisely, the parameter's of the HMM automation and of the prediction matrices $\beta_k$ of the experts $\mathcal{E}_k$, k=1, ..., K are estimated.

The neural signals acquired by the interface during the calibration phase undergo pre-treatment, in order to obtain the observation variable x(t).

This pre-treatment may include subtraction from of an average taken over all of the measured signals.

Then a time-frequency analysis of the signals thus obtained is carried out. This analysis is carried out on a moving observation window of width $\Delta T$ for all of the electrodes with the window moving by $\delta T$ between two successive positions. The time-frequency analysis is advantageously decomposition into wavelets.

Thus, with each instant $t=n\delta T$ there is a vector x(t) of size M=SPQ associated, where $S=\Delta T/\delta T$, P is the number of electrodes and $Q$ is the number of wavelets (or of frequency bands) used in the decomposition.

In parallel, kinematic parameters for the motion associated with the neural activity are acquired (for example the components of the speed at a point or the coordinates of a point). The position can be determined using a motion tracking system and the speed components are deuced from it. Conversely, the acceleration and/or the speed can be measured by a sensor (accelerometers) and the position can be deduced from these. In the case of an imagined motion (by a healthy subject) the kinematic parameters are those of the motion instructions provided to the subject. Finally, in the case of a motion presented to a subject (mirror neurons theory), in particular to a paralysed subject, the kinematic parameters are those of the presented motion.

During this learning phase, it is equally possible to determine (for example by means of thresholding of the speed) the idle states and the active states. The preparatory states may be determined through intervals of predetermined length before the start of the active states.

Thus a set of observation data is available which allows estimation of the parameters of the HMM model and the prediction matrices of the experts using a supervised or semi-supervised learning method, as explained above. The mixture coefficients are also estimated from the expression (7).

Finally the automation state is initialised, for example at an idle state.

In step 220, neural signals are continuously acquired from the P electrodes and pre-treatment of these signals is carried out which is the same as that described for the calibration phase. An observation variable (vector) x(t) is obtained at a plurality of successive instants.

At step 230, the mixture coefficients $g_k(t)$, k=1, ..., K are iteratively estimated from the past sequence of observation vectors x[1:t] using the forward algorithm. The use of the forward algorithm is particularly advantageous here insofar as it can be used to calculate the mixture coefficients without a lag time, unlike the Viterbi algorithm.

At step 240, each of the experts $E_k$, k=1, ..., K, performs a linear prediction of the command, $\hat{y}_k(t)$, by assuming that the automation is in the state $z_k$ at the instant t, that is $\hat{y}_k(t)$.

At step 250, a combination of the predictions of the K experts is made by weighting them with the mixture coefficients, $g_k(t)$. Thus an estimate of the command variable, $\hat{y}_k(t)$, is obtained. This command can be used to move an external element such as a portion of prosthetic or a cursor on a screen, for example. In this case, where the command variable comprises components relating to distinct elements, each of the elements is commanded by the corresponding component.

Figure 3:
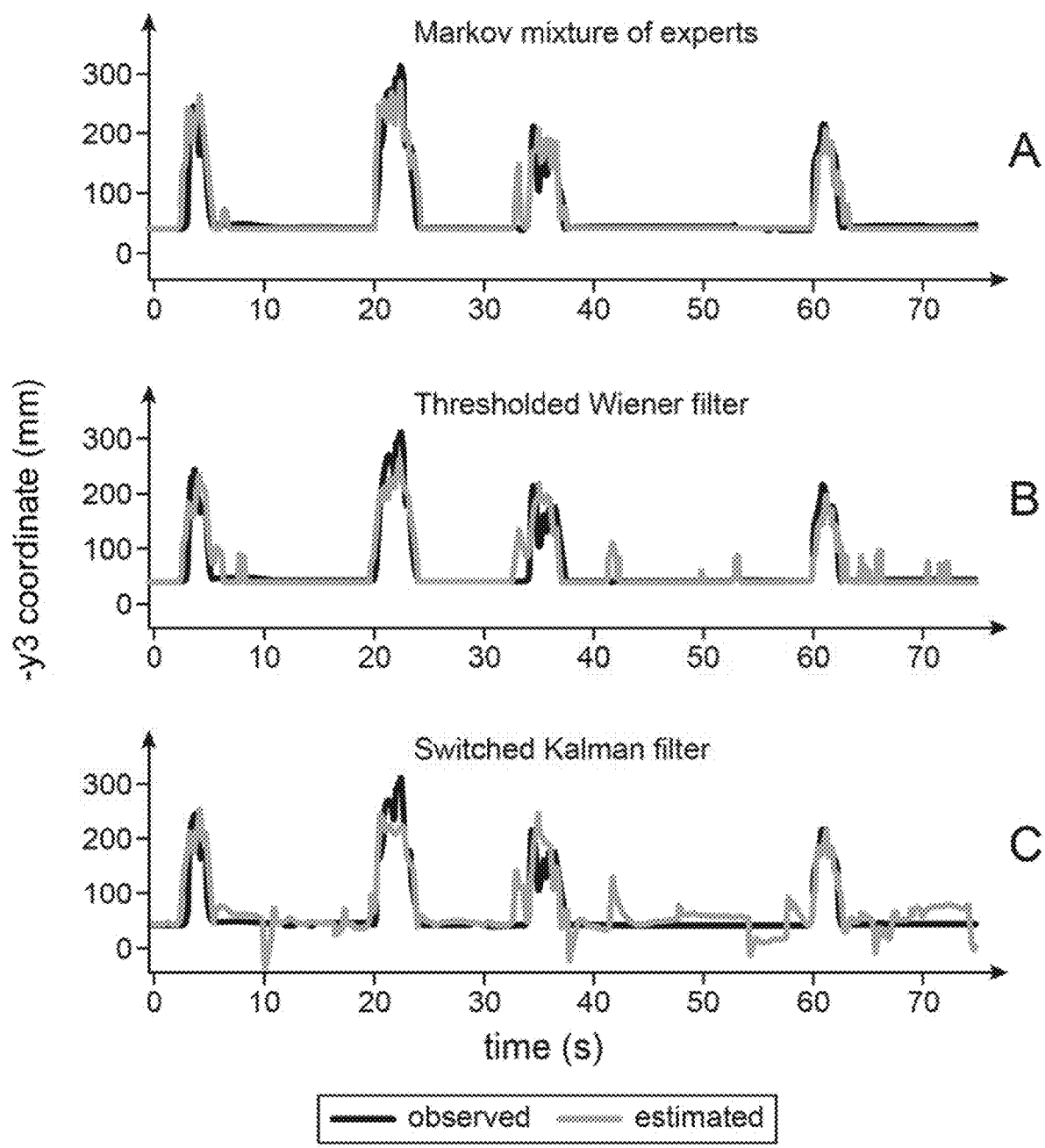
FIG. 3 shows examples of continuous decoding of motion according to different methods of the prior art and according to the method in FIG. 2.

FIG. 3 shows examples of continuous decoding of motion according to different methods of the prior art and according to the method in FIG. 2.

The various methods have been used to decode the movement of a primate's wrist from ECoG signals, during a food grasping task. The ECoG signals are acquired using a matrix (of 32 or 64 electrodes) and sampled at a frequency of 1 kHz. The characteristics of the neural signals were obtained by a Complex Continuous Wavelet Transform (or CCWT) applied to each observation window. The frequency analysis was carried out from 1 to 250 kHz with sampling in the frequency domain being carried out by a mother wavelet and 38 daughter wavelets. The observation window had a duration of 1 second and the running movement step was 100 ms.

The kinematic parameter of the motion was the three-dimensional position of the wrist.

The states used were the wrist at rest ($Z_0$) and the wrist in motion ($Z_1$).

For each of the methods, the continuous decoding was trained (calibration phase) over 70% of the duration of the session and provided an estimate of the motion over the remaining duration.

The continuous decoding of the motion was carried out according to three methods.

The first method, MML (Markov Mixture of Linear Experts), represented in line A, is that described in relation to FIG. 2.

The second method, W-TH, represented in line B, consisted of a partial least squares regression assuming a linear relationship between the kinematic parameters and the observation variable. The estimation of the states (idle, active) was carried out retrospectively by comparing the speed with a threshold.

The third model, SKF, represented in line C is a switched Kalman filter, as mentioned in the introductory part.

It can be seen that estimation of the motion in accordance with the MML method is substantially better than that in accordance with the W-TH method or the SKF method, in the sense that it conforms better to the observed motion. Furthermore, the motion estimated by the MML method only exhibits relatively few jerks. Finally the rate of false positives and of false negatives were respectively 11% and 6.9% for the W-TH method, 21.9% and 263% for the SKF method and 5.5% and 5.7% for the MML method. Thus it can be seen that the MML method allows continuous decoding of motion to be carried out with a low level of error in the prediction of active/idle states.

The invention claimed is:

1. A method of continuous decoding of motion for a direct neural interface which acquires neural signals using a plurality of electrodes, wherein a command variable, y(t), is estimated which represents kinematic motion variables, using a mixture of experts, each expert being associated with one of the hidden states of a HMM model which models an observation variable represented by an observation vector, x(t), where the HMM model comprises at least one active state and one idle state, said method comprising:
   a calibration phase for estimating parameters of the HMM model and of a linear prediction parameter of each expert;
   pre-treatment of neural signals, said treatment including a time-frequency transformation over a moving observation window, in order to obtain a sequence of observation vectors x[1:t];
   estimating the mixture coefficients ($g_k(t)$,k=1, ..., K) of the various experts from the probability of said sequence of observation vectors (P(x[1:t])) and from the probability of the respective states associated with these experts, given said sequence (P($z_k(t)$=1|x[1:t]));
   estimating by each expert, $E_k$, said motion variable from the running observation vector (x(t)) and the linear prediction parameter of said expert;
   combining estimates of the various experts using mixing coefficients in order to provide an estimate of the command variable; and
   wherein the mixture coefficient $g_k(t)$ associated with the expert $E_k$ is obtained by $$g_k(t) = \frac{P(z_k, x[1:t])}{P(x[1:t])}$$

where (P(x[1:t]) is the observation probability of the sequence of observation vectors and (P($z_k$,x[1:t])) is the state probability associated with the expert, given the sequence observed, with the probabilities (P(x[1:t])) and (P($z_k$,x[1:t])) being obtained using a forward algorithm.

2. The method of continuous decoding of motion for a direct neural interface according to claim 1, wherein the hidden states of the HMM model comprise, for each element of a plurality of elements commanded respectively by a component of the motion variable, an active state during which said element is operated and an idle state during which said element is idle.

3. The method of continuous decoding of motion for a direct neural interface according to claim 2, wherein the hidden states of the HMM module further comprise, for each of said elements, a motion preparation state which immediately succeeds an idle state and which immediately precedes an active state of said element.

4. The method of continuous decoding of motion for a direct neural interface according to claim 1, wherein, during the calibration phase, the HMM model parameters and expert linear parameters are obtained from a sequence of observation vectors and a sequence of motion variable measurements, according to a supervised learning method.

5. The method of continuous decoding of motion for a direct interface according to claim 4, wherein the linear parameters of the experts are obtained with a partial least squares regression.

6. The method of continuous decoding of motion for a direct interface according to claim 4, wherein the linear parameters of the experts are obtained with a generalised partial least squares regression.

7. The method of continuous decoding of motion for a direct neural interface according to claim 1, wherein, during the calibration phase, the HMM model parameters and linear parameters of the experts are obtained from a sequence of observation vectors and a sequence of motion variable measurements, according to a semi-supervised learning method.

8. The method of continuous decoding of motion for a direct neural interface according to claim 7, wherein the linear parameters of the experts are obtained with an expectation-maximisation algorithm.

9. The method of continuous decoding of motion for a direct neural interface according to claim 1, wherein, during the calibration phase, the HMM model parameters and linear parameters of the experts are obtained from a sequence of observation vectors and a sequence of motion variable measurements, according to a non-supervised learning method.

10. The method of continuous decoding of motion for a direct neural interface according to claim 9, wherein the parameters of the HMM model and the linear parameters of the experts are obtained with an expectation-maximisation algorithm.

11. The method of continuous decoding of motion for a direct neural interface according to claim 1, wherein the time-frequency transformation is decomposition into wavelets.

12. The method of continuous decoding of motion for a direct neural interface according to claim 1, wherein the estimate $\hat{y}_k(t)$ of the variable of motion by the expert $E_k$ is obtained by $\hat{y}_k(t)=\beta_k x(t)$ where $\beta_k$ is a matrix of size N×M where M is the dimension of the observation vectors and N the dimension of the command variable.

13. The method of continuous decoding of motion for a direct neural interface according to claim 1, wherein the neural signals are electro-cortical signals.

* * * * *